United States Patent [19]

Sandefur et al.

[11] Patent Number: 4,620,006
[45] Date of Patent: Oct. 28, 1986

[54] ACID SALTS OF 1-(CYANOALKYL)-4-GUANYLPIPERAZINES

[75] Inventors: Louise O. Sandefur; Wojciech Slusarek, both of Rochester; Burton D. Wilson, Webster; Cataldo A. Maggiulli, Pittsford, all of N.Y.

[73] Assignee: Eastman Kodak Company, Rochester, N.Y.

[21] Appl. No.: 407,215

[22] Filed: Aug. 11, 1982

[51] Int. Cl.$^4$ ............................................. C07D 295/12
[52] U.S. Cl. ...................................... 544/402; 514/252; 544/230; 544/295; 544/296
[58] Field of Search ................................. 544/295, 402

[56] References Cited

U.S. PATENT DOCUMENTS

| | | | |
|---|---|---|---|
| 2,227,158 | 3/1942 | Sexton | 544/402 |
| 2,425,341 | 8/1947 | Paden et al. | 260/564 |
| 2,904,536 | 9/1959 | Reith | 544/402 |
| 3,398,151 | 8/1968 | Wu | 544/230 |
| 3,717,634 | 2/1973 | Wu et al. | 544/230 |
| 3,907,801 | 9/1975 | Wu et al. | 424/250 |
| 3,919,230 | 11/1975 | Hill et al. | 544/295 |
| 3,976,776 | 8/1976 | Wu et al. | 424/251 |
| 4,297,495 | 10/1981 | Esanu | 544/330 |
| 4,367,335 | 1/1983 | Temple, Jr. et al. | 544/295 |

FOREIGN PATENT DOCUMENTS 51-39680 4/1976 Japan .

OTHER PUBLICATIONS

Howard et al, *J. Org. Chem.*, vol. 18, pp. 1484–1488 (1953).

Primary Examiner—Glennon H. Hollrah
Assistant Examiner—James H. Turnipseed
Attorney, Agent, or Firm—Alfred P. Lorenzo

[57] ABSTRACT

Novel 1-(cyanoalkyl)-4-guanylpiperazine acid salts are prepared by reacting novel 1-(cyanoalkyl)piperazines with cyanamide in the presence of an acid. The novel 1-(cyanoalkyl)-4-guanylpiperazine acid salts are advantageously employed to prepare 1-(cyanoalkyl)-4-(2-pyrimidyl)piperazines by reacting them with malonaldehyde in an acidic medium.

4 Claims, No Drawings

ACID SALTS OF 1-(CYANOALKYL)-4-GUANYLPIPERAZINES

BACKGROUND OF THE INVENTION

1. Field of the Invention

The invention relates to acid salts of 1-(cyanoalkyl)-4-guanylpiperazines, methods for their preparation, and methods for their use in preparing 1-(cyanoalkyl)-4-(2-pyrimidyl)piperazines (which are in turn useful materials for producing compounds having pharmacological utility as tranquilizing and anti-emetic agents).

2. Description Relative to the Prior Art

It is known that 8-[ω-[4-(2-pyrimidyl)-1-piperazinyl]alkyl]-8-azaspiro[4.5]decane-7,9-diones represented by the structural formula

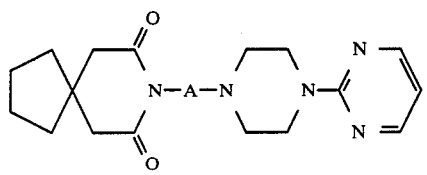

Formula I wherein A represents an alkylene group having from 2 to 6 carbon atoms, have pharmacological utility as tranquilizing and anti-emetic agents.

Methods are also known for preparing the compounds of Formula I by using, as starting materials, 1-(cyanoalkyl)-4-(2-pyrimidyl)piperazines represented by the structural formula

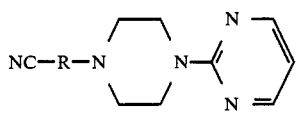

Formula II wherein R represents an alkylene group having from 1 to 5 carbon atoms. Such methods are described, for example, in U.S. Pat. Nos. 3,976,776; 3,907,801; 3,717,634; and 3,398,151, and the disclosures of these patents are hereby incorporated herein by reference.

The aforesaid patents, taken with Howard et al, *J. Org. Chem.*, Vol. 18, pp. 1484-1488 (1953) (which is referred to therein) also describe a method for preparing the compounds of Formula II. For example, for preparing 1-(3-cyanopropyl)-4-(2-pyrimidyl)piperazine, that method includes reacting piperazine with 2-chloropyrimidine to obtain 1-(2-pyrimidyl)piperazine, which is then reacted with 3-chlorobutyronitrile to obtain the desired compound.

However, such a method has a number of drawbacks. Namely, the yields are relatively poor, and the starting material, 2-chloropyrimidine, is relatively expensive. The known method, as described in the references noted above, for producing the Formula II compounds entails a considerable waste of the expensive 2-chloropyrimidine. Part of the reason for the waste is that in reacting piperazine with 2-chloropyrimidine to obtain 1-(2-pyrimidyl)piperazine, a very significant amount of by-product comprising 1,4-bis(2-pyrimidyl)piperazine also results and must be separated out, thus wasting large amounts of 2-chloropyrimidine.

The present invention provides alternative syntheses of the Formula II compounds which do not involve 2-chloropyrimidine. The inventive syntheses involve guanidation of a novel 1-(cyanoalkyl)piperazine to form a novel 1-(cyanoalkyl)-4-guanylpiperazine acid salt, followed by a ring formation reaction to convert the guanyl group to a pyrimidyl group.

In regard to guanidation, Japanese Patent Application Publication (Kokai) No. 51-39680, published Apr. 2, 1976, describes a method of creating a guanyl substituent at one nitrogen atom of piperazine by reacting piperazine with cyanamide in an inert solvent, but it does not describe such a method for guanidating a piperazine which already has a substituent group attached to one of its nitrogen atoms.

Also, in regard to guanidation, U.S. Pat. No. 2,425,341 describes guanidation of some primary and secondary amines having dissociation constants of at least $1 \times 10^{-6}$ by slowly adding an aqueous solution of cyanamide with heating to a mixture of the amine and an acid salt of t2he amine at a pH of at least 8, but it does not describe a method for preparing a 1-(cyanoalkyl)-4-guanylpiperazine acid salt from a 1-(cyanoalkyl)piperazine.

In regard to pyrimidyl ring formation, U.S. Pat. No. 4,297,495 describes a method of preparing 2-isopropylamino pyrimidine by reacting bis(isopropylguanidine)sulfate with 1,1,3,3-tetraethoxypropane in acidic aqueous solution, but it does not describe such a method for preparation of a 1-(cyanoalkyl)-4-(2-pyrimidyl)piperazine from a 1-(cyanoalkyl)-4-guanylpiperazine acid salt.

It should be noted that we also have invented other alternative syntheses of Formula II compounds and have invented other novel compounds which are useful in these syntheses. These other inventions are described in our co-pending U.S. patent applications, Ser. No. 407,216, filed Aug. 11, 1982, entitled "Cyanoalkylpiperazines and Methods for Their Preparation and Use" (now U.S. Pat. No. 4,515,947 issued May 7, 1985) and Ser. No. 407,223, filed Aug. 11, 1982, entitled "2-Pyrimidyl Alkanesulfonates and Methods for Their Preparation and Use," the disclosures of which are hereby incorporated herein by reference.

SUMMARY OF THE INVENTION

The invention provides a new method for preparing 1-(cyanoalkyl)-4-(2-pyrimidyl)piperazines. The new method includes new intermediate methods and compounds.

The new compounds of the invention are acid salts of 1-(cyanoalkyl)-4-guanylpiperazines and are represented by the structural formula

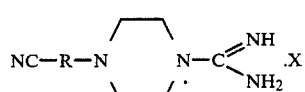

Formula III wherein R represents an alkylene group having from 1 to 5 carbon atoms and x represents an acid.

One of the new methods of the invention is a method for preparing a compound represented by Formula III. The method comprises reacting a 1-(cyanoalkyl)piperazine represented by the structural formula

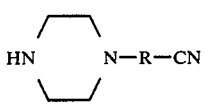

Formula IV wherein R is as previously defined, with cyanamide in the presence of the acid, x, to form a Formula III 1-(cyanoalkyl)-4-guanylpiperazine acid salt.

Another of the new methods of the invention is a method for preparing a 1-(cyanoalkyl)-4-(2-pyrimidyl)-piperazine represented by Formula II, starting with one of the new compounds of Formula III. The method comprises reacting a 1-(cyanoalkyl)-4-guanylpiperazine acid salt of Formula III with malonaldehyde in an acidic medium to form a Formula II compound. Malonaldehyde is also referred to in the art by the name propanedialdehyde and is represented by the formula $OHC-CH_2-CHO$.

A third method of the invention comprises a sequential combination of the two new methods described above. The method is one for preparing a 1-(cyanoalkyl)-4-(2-pyrimidyl)piperazine of Formula II, starting with a cyanoalkylpiperazine represented by Formula IV. The method comprises reacting a Formula IV cyanoalkylpiperazine with cyanamide in the presence of an acid to form a 1-(cyanoalkyl)-4-guanylpiperazine acid salt represented by Formula III and then reacting the Formula III compound in an acidic medium with malonaldehyde to form a 1-(cyanoalkyl)-4-(2-pyrimidyl)piperazine represented by Formula II.

DESCRIPTION OF PREFERRED EMBODIMENTS

The invention is described in detail below mainly in regard to specific preferred embodiments, wherein the alkylene group represented by R in Formulas II, III, and IV is a propylene group. Those are the specific embodiments that are involved in making use of the present invention in a reaction sequence to ultimately produce 8-[4-[4-(2-pyrimidyl)-1-piperazinyl]butyl]-8-azaspiro[4.5]decane-7,9-dione, a compound which also has been referred to in the prior art by the name buspirone and is known to be a particularly good tranquilizing and anti-emetic agent among those of Formula I. It is a particular purpose of the invention to provide alternative routes for production of buspirone. However, unless otherwise stated below, it should be understood that any discussions of general or preferred reaction conditions, reagents, optional procedures, etc. are equally applicable to the remaining embodiments within the scope of the claimed invention, wherein the alkylene group represented by R is other than propylene.

Of the new compounds of the invention represented by Formula III, particularly preferred embodiments are the 1-(3-cyanopropyl)-4-guanylpiperazine acid salts, because of their utility in preparing buspirone.

In accordance with a method of the invention, a Formula III 1-(cyanoalkyl)-4-guanylpiperazine acid salt is prepared by reacting a Formula IV cyanoalkylpiperazine with cyanamide in the presence of an acid under conditions sufficient to form the corresponding Formula III compound. Thus, in some particularly preferred embodiments a 1-(3-cyanopropyl)-4-guanylpiperazine acid salt is prepared by reacting 1-(3-cyanopropyl)piperazine with cyanamide in the presence of an acid.

The Formula IV cyanoalkylpiperazines used in this method are themselves novel compounds, produced by novel methods, e.g., by reaction of an excess of piperazine with a haloalkylnitrile in the presence of an acid acceptor under conditions sufficient to form the Formula IV compound as the major product. A novel method of preparing a novel cyanoalkylpiperazine is described in more detail in Example 1 below. Such novel compounds and methods are also described in our copending U.S. patent application, Ser. No. 407,216, filed Aug. 11, 1982, now U.S. Pat. No. 4,515,947 entitled "Cyanoalkylpiperazines and Methods for Their Preparation and Use."

The acid used in this method for preparing a Formula III compound from a Formula IV compound, becomes the acid salt portion of the Formula III compound. The acid is preferably chosen from readily available mineral acids (e.g., hydrochloric acid, nitric acid, or sulfuric acid) and lower aliphatic carboxylic acids (e.g., acetic acid). Of these, sulfuric acid and acetic acid are preferred. When the acid is a dibasic acid, such as sulfuric acid, one molecule of acid will associate with two molecules of 1-(cyanoalkyl)-4-guanylpiperazine in the product acid salt.

The method is preferably carried out in an organic solvent, inert to the reaction. Typical organic solvents, such as acetone, ethyl acetate, and lower alkanols having from 1 to 3 carbon atoms are adequate. Isopropanol is a preferred solvent.

Cyanamide is used in the method in either anhydrous or aqueous form. In order to achieve best yields of Formula III compound from Formula IV compound, it is preferable to include cyanamide in excess of the stoichiometric amount for the reaction. For example, in some embodiments cyanamide is included in about twice the stoichiometric amount. Exact proportions to be used for maximum yield will vary depending on the specific compounds being used.

In carrying out the method for producing Formula III compounds from Formula IV compounds, the reactants are simply heated together in solvent at reflux until the reaction is complete.

In accordance with another method of the invention, a Formula II 1-(cyanoalkyl)-4-(2-pyrimidyl)piperazine is prepared by reacting a Formula III compound with malonaldehyde in an acidic medium under conditions sufficient to form the Formula II compound. In some particularly preferred embodiments a 1-(3-cyanopropyl)-4-guanylpiperazine acid salt is reacted with malonaldehyde in an acidic medium to produce 1-(3-cyanopropyl)-4-(2-pyrimidyl)piperazine. This compound is particularly useful as a starting material for producing buspirone by the method described in the patents incorporated herein by reference above.

While the malonaldehyde used in this method can be prepared ahead of time and then be brought into reactive contact with the Formula III compound in the acidic medium, malonaldehyde is an unstabale compound which undergoes degradation in a short period of time. Therefore, it is preferable and more convenient in this method to generate malonaldehyde in situ in the acidic medium.

If one wishes to prepare the malonaldehyde ahead of time, this is accomplished, e.g., by reacting a 1,1,3,3-tetraalkoxypropane represented by the structural formula

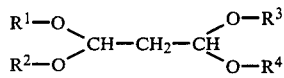

Formula V (wherein $R^1$, $R^2$, $R^3$, and $R^4$ are the same or different and represent alkyl groups having from 1 to 3 carbon atoms) with an acidic medium to form malonaldehyde. The malonaldehyde can then be extracted from the acidic medium with an organic solvent and can be stored in that solvent until used. However, it cannot be stored very long, because it will quickly degrade during storage and become useless for the inventive method.

It is much simpler to carry out the inventive method by using a Formula V tetraalkoxypropane as a starting material to generate malonaldehyde in situ, rather than starting with previously prepared malonaldehyde. In carrying out the inventive method of preparing a Formula II compound in this preferable manner, a Formula III compound and a Formula V compound are brought together in an acidic medium and simply stirred until the reactions are complete. The reactions which occur are, first, reaction of the Formula V compound with the acidic medium to form malonaldehyde, and, second, reaction of the malonaldehyde, the Formula III compound, and the acidic medium to form a Formula II compound. The medium can then be neutralized and the Formula II compound isolated by extraction with an organic solvent, such as ethyl acetate, followed by distillation.

The Formula V 1,1,3,3-tetraalkoxypropanes useful in this method are easily prepared and readily available commercially. For example, 1,1,3,3-tetramethoxypropane can be purchased from Eastman Kodak Company, Rochester, N.Y., and it is particularly preferred for use in this method, because of its relatively low cost and minimal steric hindrance.

The acidic medium for this method is preferably an aqueous solution of any readily available mineral acid. An acidic medium is necessary to promote hydrolysis of the alkoxy groups of the Formula V compound to form malonaldehyde and to initiate the ring formation reaction between malonaldehyde and the Formula III compound.

In accordance with a third method of the invention, the two methods described above are carried out in sequence to produce a Formula II 1-(cyanoalkyl)-4-(2-pyrimidyl)piperazine starting with a Formula IV cyanoalkylpiperazine. For example, in a particularly preferred embodiment of the method 1-(3-cyanopropyl)-piperazine is reacted with cyanamide in the presence of sulfuric acid to form 1-(3-cyanopropyl)-4-guanylpiperazine sulfate. This product is then reacted with malonaldehyde in an aqueous acidic medium to produce 1-(3-cyanopropyl)-4-(2-pyrimidyl)piperazine.

All preferred conditions, reagents, etc. for the steps of the inventive method of producing Formula II compounds from Formula IV compounds are the same as those recited previously in the detailed description, hereinabove, of those steps as individual inventive methods.

The following Examples are presented to further illustrate some preferred embodiments of the invention.

EXAMPLE 1

Preparation of 1-(3-Cyanopropyl)-4-guanylpiperazine Sulfate from 1-(3-Cyanopropyl)piperazine In a 1000 ml., 3-necked, round-bottomed flask, equipped with an addition funnel, a stirrer and a thermometer, was placed 250 ml. of isopropanol and 30.6 g. (0.2 mole) of 1-(3-cyanopropyl)piperazine. To this solution, stirred in an ice-water bath, 9.8 g. (0.1 mole) of sulfuric acid was added in drops at a rate that kept the temperature at 25°–30° C., followed by addition of 16.8 g. (0.4 mole) of cyanamide in one portion. The addition funnel was then replaced with a reflux condenser, and the mixture was refluxed for 26 hours, stirred at room temperature (about 23° C.) for 15 hours, and filtered. The collected solid was washed with two 20 ml. portions of isopropanol and dried in vacuo over phosphorus pentoxide at room temperature for 2 days. The yield of 1-(3-cyanopropyl)-4-guanylpiperazine sulfate melting point: 240°–242° C.) was 43.9 g. (0.18 mole; 90%). The structure of the product was verified by IR and TLC analytical techniques.

This method has also been carried out successfully (yields: 84–96%) using different acids (e.g., acetic acid) and/or different solvents (e.g., ethanol).

The 1-(3-cyanopropyl)piperazine used in this Example was prepared as follows:

In a 5-liter 4-necked flask, equipped with an efficient stirrer, thermometer, condenser, and addition funnel, a slurry of 1292 g. (15.0 moles) piperazine and 930 g. (7.5 moles) sodium carbonate in 2.0 liters of ethyl acetate was stirred and heated to reflux (86° C.). The heat source was removed and from the funnel 975 g. (ca. 7.5 moles) of a mixture, comprising by weight about 60% 3-chlorobutyronitrile, about 35% 3-bromobutyronitrile, and the remainder glutaronitrile, was added at such a rate that a gentle reflux was maintained. Approximately one hour was required. Gas evolution ($CO_2$) was moderate during the addition but increased subsequently. The slurry was stirred and heated until the reaction was complete.

The reaction mixture was filtered, and the resulting solid cake was pressed down under a rubber dam. The solids were washed twice by slurrying in 1-liter portions of ethyl acetate. The combined filtrates were concentrated under vacuum to remove solvent and then the bulk of the excess piperazine. Finally the pot was heated to 150°–170° C. to distill the rest of the piperazine.

The product was subsequently distilled under high vacuum to give 1-(3-cyanopropyl)piperazine (melting point: 102.5°–103.5° C.), the structure of which was verified by IR, NMR, and TLC analytical techniques. The total yield was 796 g. or 69.3% of the theoretical 1149 g. of 1-(3-cyanopropyl)piperazine.

The pot residue was found to comprise 1,4-bis(3-cyanoproypyl)piperazine by-product.

EXAMPLE 2

Preparation of 1-(3-Cyanopropyl)-4-(2-pyrimidyl)piperazine from 1-(3-Cyanopropyl)-4-guanylpiperazine Sulfate To a solution of 61.0 g. (0.25 mole) of 1-(3-cyanopropyl)-4-guanylpiperazine sulfate in 200 ml. of 50% sulfuric acid, stirred in a 1000 ml. round-bottomed flask, was added, at 10°–15° C., 43.1 g. (0.263 mole) of 1,1,3,3-tetramethoxypropane during 5 minutes. The resulting solution was stirred at room temperature for 18 hours and then poured onto 1000 ml. of ice. The mixture was neutralized with 225 ml. of 50% NaOH (pH 10-12). More ice was added during neutralization to keep the temperature at 25°-30° C. Final volume was 1800 ml. This mixture was extracted with 3×300 ml. of ethyl acetate. The extracts were washed with 200 ml. of a saturated aqueous solution of NaCl, stirred for ½ hour with magnesium sulfate and a decolorizing carbon, filtered and evaporated under aspirator pressure. The residual oil was distilled in vacuo. The fraction boiling at 143°-146° C./0.15 mm Hg was collected. The yield of 1-(3-cyanopropyl)-4-(2-pyrimidyl)piperazine was 23.5 g. (0.102 mole; 41%). The structure of the product was verified by IR analysis.

The invention has been described in detail with particular reference to certain preferred embodiments thereof, but it will be understood that variations and modifications can be effected within the spirit and scope of the invention.

What is claimed is:

1. A 1-(cyanoalkyl)-4-guanylpiperazine acid salt represented by the structural formula

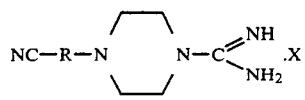

wherein R represents an alkylene group having from 1 to 5 carbon atoms and x represents an acid.

2. The 1-(cyanoalkyl)-4-guanylpiperazine acid salt of claim 1, wherein R represents a propylene group.

3. The 1-(cyanoalkyl)-4-guanylpiperazine acid salt of claim 1, wherein x represents sulfuric acid or acetic acid.

4. The 1-(cyanoalkyl)-4-guanylpiperazine acid salt of claim 1, wherein R represents a propylene group and X represents sulfuric acid.

* * * * *